United States Patent
Feke et al.

(10) Patent No.: US 8,050,735 B2
(45) Date of Patent: *Nov. 1, 2011

(54) APPARATUS AND METHOD FOR MULTI-MODAL IMAGING

(75) Inventors: Gilbert Feke, Durham, CT (US); Douglas Lincoln Vizard, Durham, CT (US); William E. McLaughlin, Guilfort, CT (US)

(73) Assignee: Carestream Health, Inc., Rochester, NY (US)

( * ) Notice: Subject to any disclaimer, the term of this patent is extended or adjusted under 35 U.S.C. 154(b) by 122 days.

This patent is subject to a terminal disclaimer.

(21) Appl. No.: 12/354,830

(22) Filed: Jan. 16, 2009

(65) Prior Publication Data

US 2009/0159805 A1 Jun. 25, 2009

Related U.S. Application Data

(63) Continuation-in-part of application No. 11/221,530, filed on Sep. 8, 2005, now Pat. No. 7,734,325.

(60) Provisional application No. 61/024,621, filed on Jan. 30, 2008.

(51) Int. Cl.
*A61B 6/00* (2006.01)

(52) U.S. Cl. .......... 600/407; 600/425; 600/476; 378/44; 250/336.1; 250/339.06

(58) Field of Classification Search .................. 250/367; 382/132, 264; 378/62; 600/407
See application file for complete search history.

(56) References Cited

U.S. PATENT DOCUMENTS

| | | | |
|---|---|---|---|
| 1,609,703 A | 12/1926 | Eggert et al. | |
| 3,717,764 A | 2/1973 | Fujimura et al. | |
| 3,936,644 A | 2/1976 | Rabatin | |
| 4,028,550 A | 6/1977 | Weiss et al. | |
| 4,088,894 A | 5/1978 | Rabatin | |
| 4,107,070 A | 8/1978 | Everts et al. | |

(Continued)

FOREIGN PATENT DOCUMENTS

EP 1 111 625 A2 6/2001

(Continued)

OTHER PUBLICATIONS

Zhang et al., "Monomolecular Multimodal Fluorescence-Radioisotope Imaging Agents," Bioconjugate Chemistry, 16(5), pp. 1232-1239, 2005.

(Continued)

*Primary Examiner* — Tse Chen
*Assistant Examiner* — Vani Gupta

(57) ABSTRACT

An imaging system for imaging an object, including: a support member adapted to receive the object in an immobilized state; a removable phosphor plate assembly adapted to respond to ionizing radiation by emitting visible light; first imaging means for imaging the immobilized object in a first imaging mode to capture a first image; second imaging means for imaging the immobilized object in a second imaging mode, different from the first imaging mode, to capture a second image; and third imaging means for imaging the immobilized object in a third imaging mode, different from the first and second imaging modes, to capture a third image, wherein the first imaging mode uses the phosphor plate assembly and is selected from the group: x-ray mode and low energy radio isotope mode; the second imaging mode uses the phosphor plate assembly and a high energy radio isotope mode, and the third imaging mode is selected from the group: bright-field mode, fluorescence mode and luminescence mode.

20 Claims, 7 Drawing Sheets

U.S. PATENT DOCUMENTS

| | | | |
|---|---|---|---|
| 4,208,470 A | 6/1980 | Rabatin | |
| 4,232,227 A | 11/1980 | Finkenzeller et al. | |
| 4,394,737 A | 7/1983 | Komaki et al. | |
| 4,446,365 A | 5/1984 | Ong et al. | |
| 4,675,529 A | 6/1987 | Kushida | |
| 4,710,637 A | 12/1987 | Luckey et al. | |
| 4,829,188 A | 5/1989 | Shinomiya et al. | |
| 4,870,279 A | 9/1989 | Cueman et al. | |
| 4,891,527 A | 1/1990 | Rabatin | |
| 4,898,175 A | 2/1990 | Noguchi | |
| 5,069,982 A | 12/1991 | Zegarski | |
| 5,501,225 A | 3/1996 | Wilson | |
| 5,534,709 A | 7/1996 | Yoshimoto et al. | |
| 5,650,135 A | 7/1997 | Contag et al. | |
| 5,663,005 A | 9/1997 | Dooms et al. | |
| 5,717,791 A | 2/1998 | Labaere et al. | |
| 5,748,768 A | 5/1998 | Sivers et al. | |
| 5,830,629 A | 11/1998 | Vizard et al. | |
| 6,227,704 B1 | 5/2001 | Bani-Hashemi et al. | |
| 6,229,873 B1 | 5/2001 | Bani-Hashemi et al. | |
| 6,269,177 B1 | 7/2001 | Dewaele et al. | |
| 6,278,765 B1 | 8/2001 | Berliner | |
| 6,346,707 B1 | 2/2002 | Vizard et al. | |
| 6,379,044 B1 | 4/2002 | Vastenaeken et al. | |
| 6,416,800 B1 | 7/2002 | Weber et al. | |
| 6,424,750 B1 | 7/2002 | Colbeth et al. | |
| 6,444,988 B1 | 9/2002 | Vizard | |
| 6,447,163 B1 | 9/2002 | Bani-Hashemi et al. | |
| 6,459,094 B1 | 10/2002 | Wang et al. | |
| 6,473,489 B2 | 10/2002 | Bani-Hashemi et al. | |
| 6,495,812 B1 | 12/2002 | Wurm et al. | |
| 6,615,063 B1 | 9/2003 | Ntziachristos et al. | |
| 7,113,217 B2 | 9/2006 | Nilson et al. | |
| 7,190,991 B2 | 3/2007 | Cable et al. | |
| 7,198,404 B2 | 4/2007 | Navab et al. | |
| 7,338,651 B2 | 3/2008 | Bornhop et al. | |
| 7,394,053 B2 | 7/2008 | Frangioni et al. | |
| 7,734,325 B2 * | 6/2010 | Vizard et al. | 600/407 |
| 2001/0012386 A1 | 8/2001 | Struye et al. | |
| 2003/0011701 A1 | 1/2003 | Nilson et al. | |
| 2003/0082104 A1 | 5/2003 | Mertelmeier | |
| 2003/0187344 A1 | 10/2003 | Nilson et al. | |
| 2003/0211158 A1 | 11/2003 | Frechet et al. | |
| 2004/0004193 A1 | 1/2004 | Nilson et al. | |
| 2004/0089817 A1 | 5/2004 | Long et al. | |
| 2004/0202360 A1 | 10/2004 | Besson | |
| 2004/0249260 A1 | 12/2004 | Wang et al. | |
| 2005/0028482 A1 | 2/2005 | Cable et al. | |
| 2005/0122529 A1 | 6/2005 | Kim et al. | |
| 2005/0148846 A1 | 7/2005 | Cable et al. | |
| 2005/0175538 A1 | 8/2005 | Coquoz et al. | |
| 2005/0237423 A1 | 10/2005 | Nilson et al. | |
| 2006/0064000 A1 | 3/2006 | Vizard et al. | |
| 2006/0111613 A1 | 5/2006 | Boutillette et al. | |
| 2006/0118742 A1 | 6/2006 | Levenson et al. | |
| 2006/0173354 A1 | 8/2006 | Ntziachristos et al. | |
| 2006/0210135 A1 | 9/2006 | Kanegae | |
| 2007/0016077 A1 | 1/2007 | Nakaoka et al. | |
| 2007/0063154 A1 | 3/2007 | Chen et al. | |
| 2007/0087445 A1 | 4/2007 | Tearney et al. | |
| 2007/0217713 A1 | 9/2007 | Milanfar et al. | |
| 2007/0238957 A1 | 10/2007 | Yared | |
| 2007/0281322 A1 | 12/2007 | Jaffe et al. | |
| 2008/0049893 A1 | 2/2008 | Bartzke et al. | |
| 2008/0281322 A1 | 11/2008 | Sherman et al. | |
| 2009/0086908 A1 | 4/2009 | Harder et al. | |
| 2009/0159805 A1 | 6/2009 | Feke et al. | |
| 2009/0238434 A1 | 9/2009 | Feke et al. | |
| 2010/0022866 A1 | 1/2010 | Feke et al. | |

FOREIGN PATENT DOCUMENTS

| | | |
|---|---|---|
| EP | 1 304 070 A2 | 4/2003 |
| EP | 1 619 548 A2 | 1/2006 |
| JP | 58-17544 U | 7/1981 |
| JP | 02-031144 | 2/1990 |
| JP | 02-052246 | 2/1990 |
| JP | 09-309845 | 12/1997 |
| JP | 11-244220 | 9/1999 |
| JP | 2001-255607 | 9/2001 |
| JP | 2001-299786 | 10/2001 |
| JP | 2003-028995 | 1/2003 |
| JP | 2004-121289 | 4/2004 |
| JP | 2005-049341 | 2/2005 |
| JP | 2005-164577 | 6/2005 |
| WO | 2004/081865 A2 | 9/2004 |
| WO | 2004/089204 A1 | 10/2004 |
| WO | 2004/108902 A2 | 12/2004 |
| WO | 2005/027730 A2 | 3/2005 |
| WO | 2007/032940 A2 | 3/2007 |

OTHER PUBLICATIONS

Research Takes Many Directions, Science, vol. 303, No. 5657, Jan. 23, 2004. Advertisement (2 pages).

Sage, Linda, "The Bare Bones of Animal Imaging", The Scientist, vol. 19, Issue 4, Feb. 28, 2005. (3 pages).

CosmoBio report, Mar. 2004, No. 43, "Kodak Image Station 2000MM". (English translation of p. 18—5 pages).

CosmoBio report, Mar. 2004, No. 43, "Kodak Image Station 2000MM". (JP language—Foreign, 13 pages).

Kodak Image Station 2000MM Multimodal Imaging System, Internet web address: http://www.kodak.com/US/en/health/scientific/products/imgstation2000MM/index.shtml-Sep 16, 2004. (1 page).

Hussain et al., Enhanced Oral Uptake of Tomato Lectin-Conjugated Nanoparticles in the Rat, Pharmaceutical Research, vol. 14, No. 5, 1997, pp. 613-618.

V.P. Torchilin, Polymer-coated long-circulating microparticulate pharmaceuticals, J. Microencapsulation, 1998, vol. 15, No. 1, pp. 1-19.

Alyautdin et al., Delivery of Loperamide Across the Blood-Brain Barrier with Polysorbate 80-Coated Polybutylcyanoacrylate Nanoparticles, Pharmaceutical Research, vol. 14, No. 3, 1997, pp. 325-328.

Y. Kwon et al., Enhanced antigen presentation and immunostimulation of dendritic cells using acid-degradable cationic nanoparticles, Journal of Controlled Release 105, 2005, pp. 199-212.

Harlow et al., Antibodies—A Laboratory Manual, Chapter 5—Immunizations, 1988, pp. 91-113.

Winter et al., Man-made antibodies, Nature—vol. 349, Jan. 24, 1991, pp. 293-299.

Köhler et al., Derivation of specific antibody-producing tissue culture and tumor lines by cell fusion, Medical Research Council Laboratory of Molecular Biology, Cambridge, Eur. J. Immunol., 1976, vol. 6, pp. 511-519.

LoBuglio et al., Mouse/human chimeric conoclonal antibody in man: Kinetics and immune response, Proc. Natl. Acad. Sci., vol. 86, Jun. 1989 Immunology, pp. 4220-4224.

De Verdiè, et al., Reversion of multidrug resistance with polyalkycyanoacrylate nanoparticles: towards a mechanism of action, BJC British Journal of Cancer, 1997, vol. 76 (2), pp. 198-205.

Sharma et al., Novel Taxol® Formulation: Polyvinylpyrrolidone Nanoparticle-Encapsulated Taxol® for Drug Delivery in Cancer Therapy, Oncology Research, vol. 8, Nos. 7/8, pp. 281-286, 1986.

Zobel et al., Cationic Polyhexylcyanoacrylate Nanoparticles as Carriers for Antisense Oligonucleotides, Antisense & Nucleic Acid Drug Development, vol. 7, 1997, pp. 483-493.

Burke et al., Acid-Base Equilibria of Weak Polyelectrolytes in Multilayer Thin Films, Langmuir, 2003, vol. 19, No. 8, pp. 3297-3303.

Hrkach et al., Nanotechnology for biomaterials engineering; structural characterization of amphiphilic polymeric nanoparticles by $^1$H NMR spectroscopy, Biomaterials, vol. 18, No. 1, 1997, pp. 27-30.

G. Volkheimer, Übersicht, Persorption von Mikropartikeln, Pathologies, 1993, vol. 14, pp. 247-252.

Moghimi et al., Nanomedicine: current status and future prospects, The FASEB Journal, vol. 19, Mar. 2005, pp. 311-330.

Soukchareun et al., Preparation and Characterization of Antisense Oligonucleotide—Peptide Hybrids Containing Viral Fusion Peptides, Bioconjugate Chem, 1995, vol. 6, pp. 43-53.

G. Kwon et al., Block copolymer micelles as long-circulating drug vehicles, Advanced Drug Delivery Reviews, vol. 16, 1995, pp. 295-309.

Labhasetwar et al., Nanoparticle drug delivery system for restenosis, Advanced Drug Delivery Reviews, vol. 24, 1997, pp. 63-85.

Co-pending USSN: U.S. Appl. No. 11/400,935, filed Apr. 10, 2006, Publication No. 2000/0238656, Harder et al., Functionalized Poly(Ethylene Glycol).

Co-pending USSN: U.S. Appl. No. 11/165,849, filed Jun. 24, 2006, Publication No. 2006/0293396, Bringley et al., Nanoparticle Based Substrate for Image Contrast Agent Fabrication.

Yamashita et al., Mist particle diameters are related to the toxicity of waterproofing sprays: Comparison between toxic and non-toxic products, vol. 39, 71-74.

Cleare et al., "An Experimental Study of the Mottle Produced by X-Ray Intensifying Screens," The Am. J. of Roent. and Rad. Physics, vol. 88, No. 1, pp. 168-174, Jul. 1962.

Nature Methods, "Harnessing multimodality to enhance quantification and reproducibility of in vivo molecular imaging data", by Gilbert D. Feke et al., Nov. 2008, 2 pages.

Biochem Biophys Res Commun, Inspiration for Life Science, "Anti Human Galectin 3 Polyelonal Antibody", by W. Zhu, 280:11831188, 2001, 2 pages.

IEEE Transactions on Nuclear Science, "Iodine 125 Imaging in Mice Using NaI(TI)/Flat Panel PMT Integral Assembly", by M.N. Cinti et al., vol. 54, No. 3, Jun. 2007, pp. 461-468.

Mat. Res. Soc. Symp. Proc., "Optimising of the Physico-Chemical Properties of a Novel Barium Sulphate Preparation for the X-Ray Examination of the Intestine", by Barbara Laermann et al., vol. 550, 1999 Materials Research Society, pp. 59-64.

Am. Assoc. Phys. Med., "MicroCT scanner performance and considerations for vascular specimen imaging", by Michael Marxen et al., Med. Phys. 31 (2), Feb. 2004, pp. 305-313.

Rat Atlas Project, Internet Study: Hubei Bioinformatics and Molecular Imaging Key Laboratory, The Key Laboratory of Biomedical Photonics of Ministry of Education, College of Life Science and Technology, Huazhong University of Science and Technology, http://202.114.29.53/vch/mice/index.aspx. (4 pages).

User's Guide for KODAK Imagst Station 2000R (172 pages).

User's Guide for KODAK Image Station 2000MM (168 pages).

Kodak Image Station 2000MM Multi-Modal Imager, Kodak Scientific Imaging Systems—advertisement—Fall/2003 (2 pages).

Proceedings of the American Thoracic Society, "Micro-Computed Tomography of the Lungs and Pulmonary-Vascular System", by Erik L. Ritman, 2 pp. 477-480, 2005.

The Journal of Nuclear Medicine, "Significance of Incidental 18F-FDG Accumulations in the Gastrointestical Tract in PET/CT: Correlation with Endoscopic and Histopathologic Results", by Ehab M. Kamel et al., vol. 45, No. 11, pp. 1804-1810, 2004.

P. Mitchell, "Picture Perfect: Imaging Gives Biomarkers New Look", *Pharma DD*, vol. 1, No. 3, pp. 1-5 (2006).

Virostko et al., Molecular Imaging, vol. 3, No. 4, Oct. 2004, pp. 333-342, Factors Influencing Quantification of In Vivo Bioluminescence Imaging: Application to Assessment of Pancreatic Islet Transplants.

Da Silva et al., ScienceDirect, Nuclear Instruments and Methods in Physics Research, Design of a small animal multiomodality tomographer for X-ray and optical coupling: Theory and experiments, 2007, pp. 118-121.

Kruger et al., HYPR-spectral photoacoustic CT for preclinical imaging, Photons Plus Ultrasound Imaging and Sensing 2009, Proc. Of SPIE, vol. 7177, 10 pages.

Corresponding WO = PCT/us2005/032504, International Preliminary Report on Patentability, dated Mar. 27, 2007, 8 pages.

Corresponding CN = CN 200580031808.5—SIPO First Office Action dated Dec. 9, 2009. 14 pages.

International Search Report, International Application No. PCT/US2005/032504, dated Dec. 23, 2005.

International Search Report, International Application No. PCT/US2008/010304, dated Dec. 8, 2008.

International Search Report, International Application No. PCT/US2009/000457, dated Aug. 21, 2009.

* cited by examiner

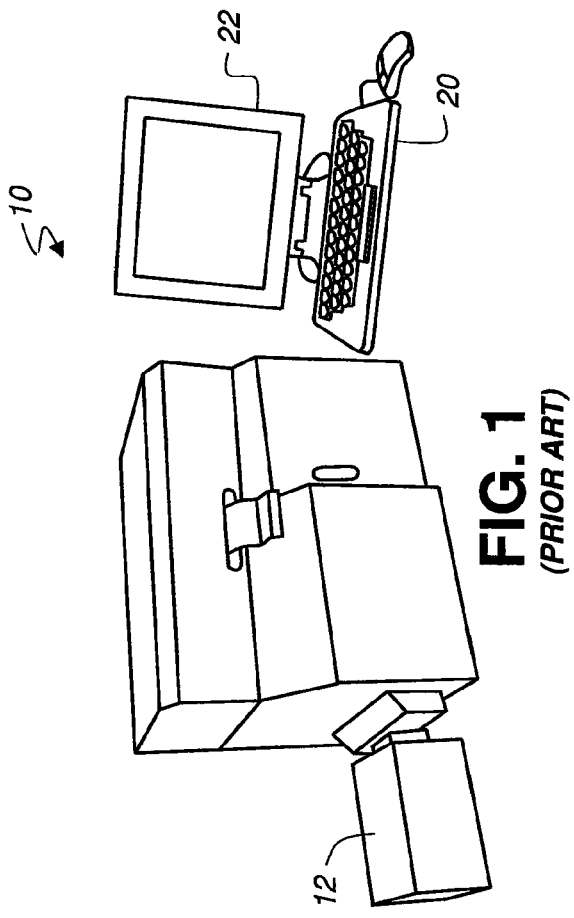
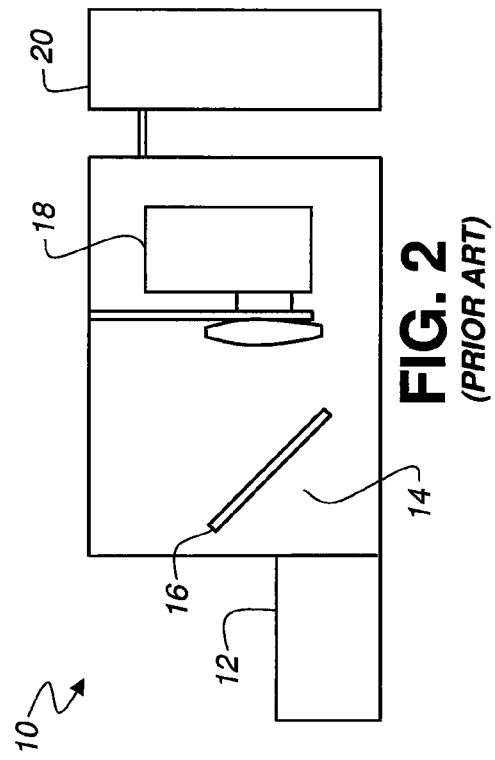
FIG. 1 (PRIOR ART)
FIG. 2 (PRIOR ART)

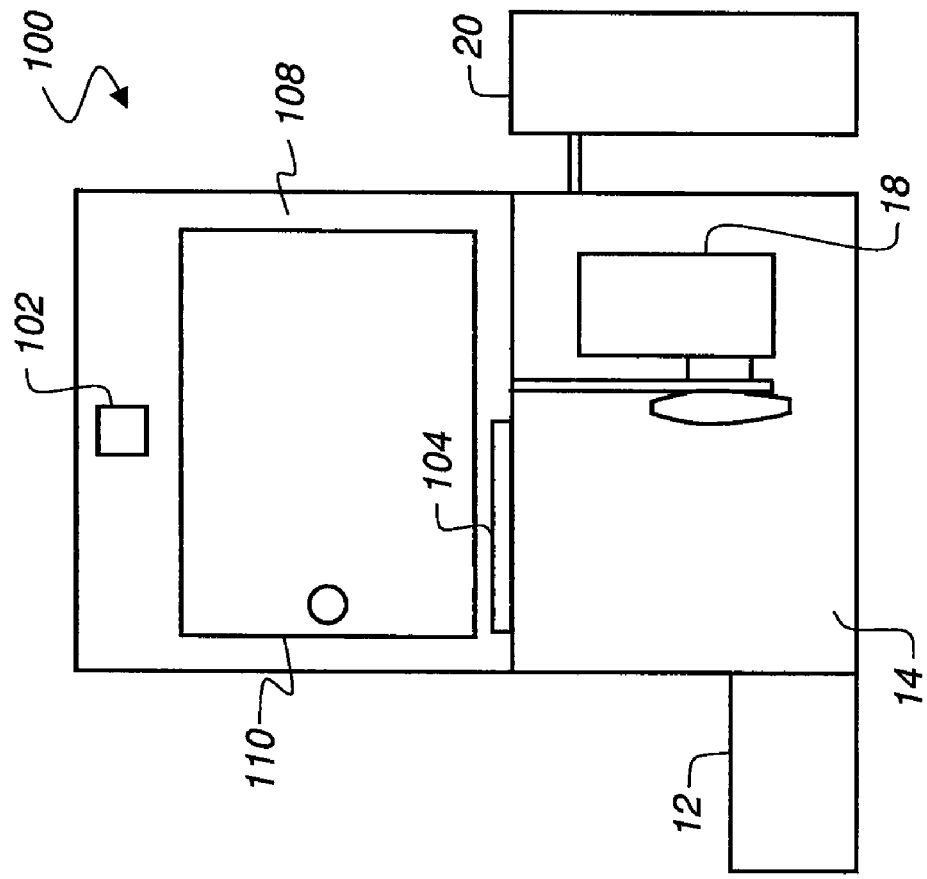
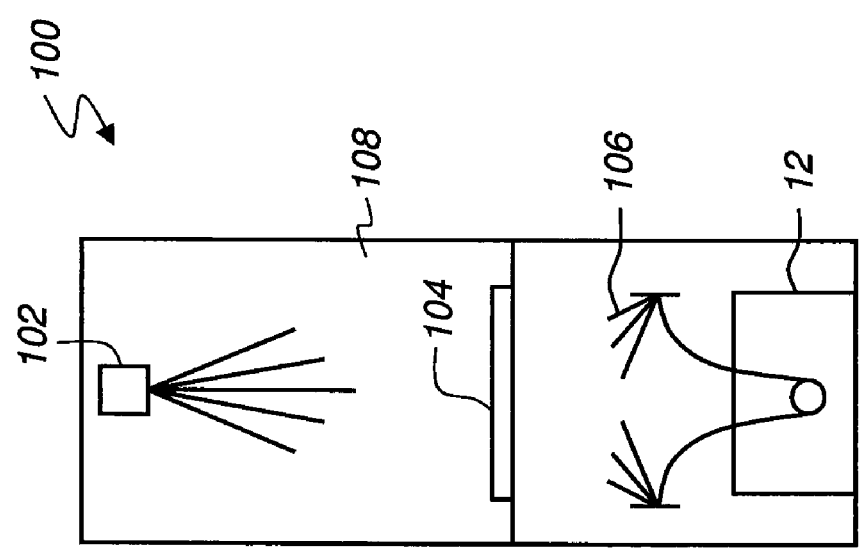

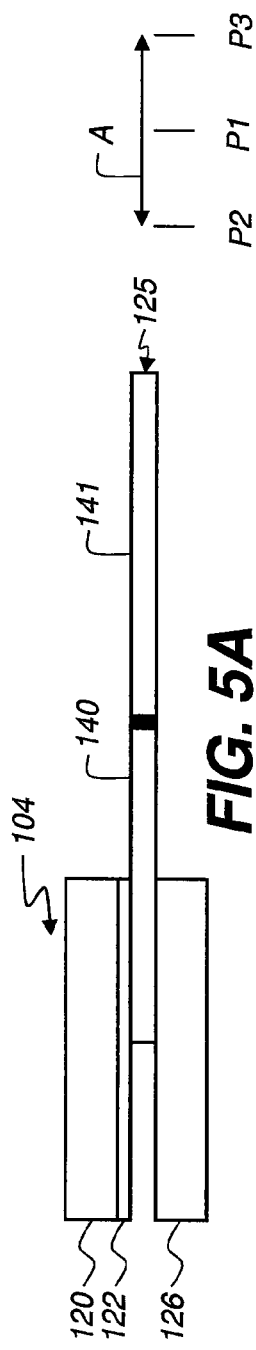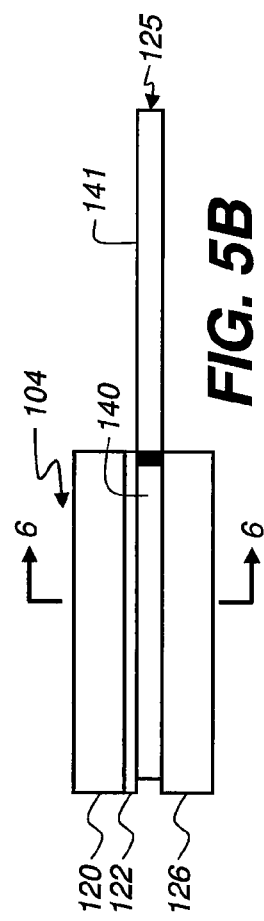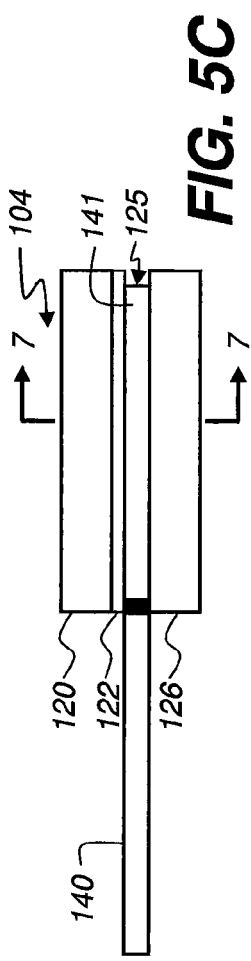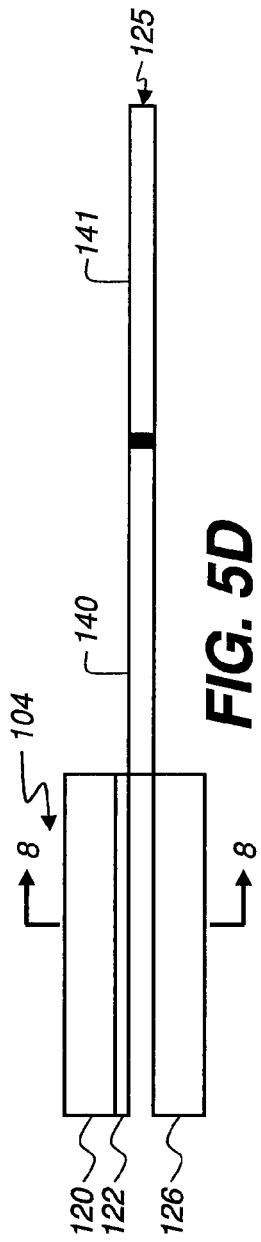

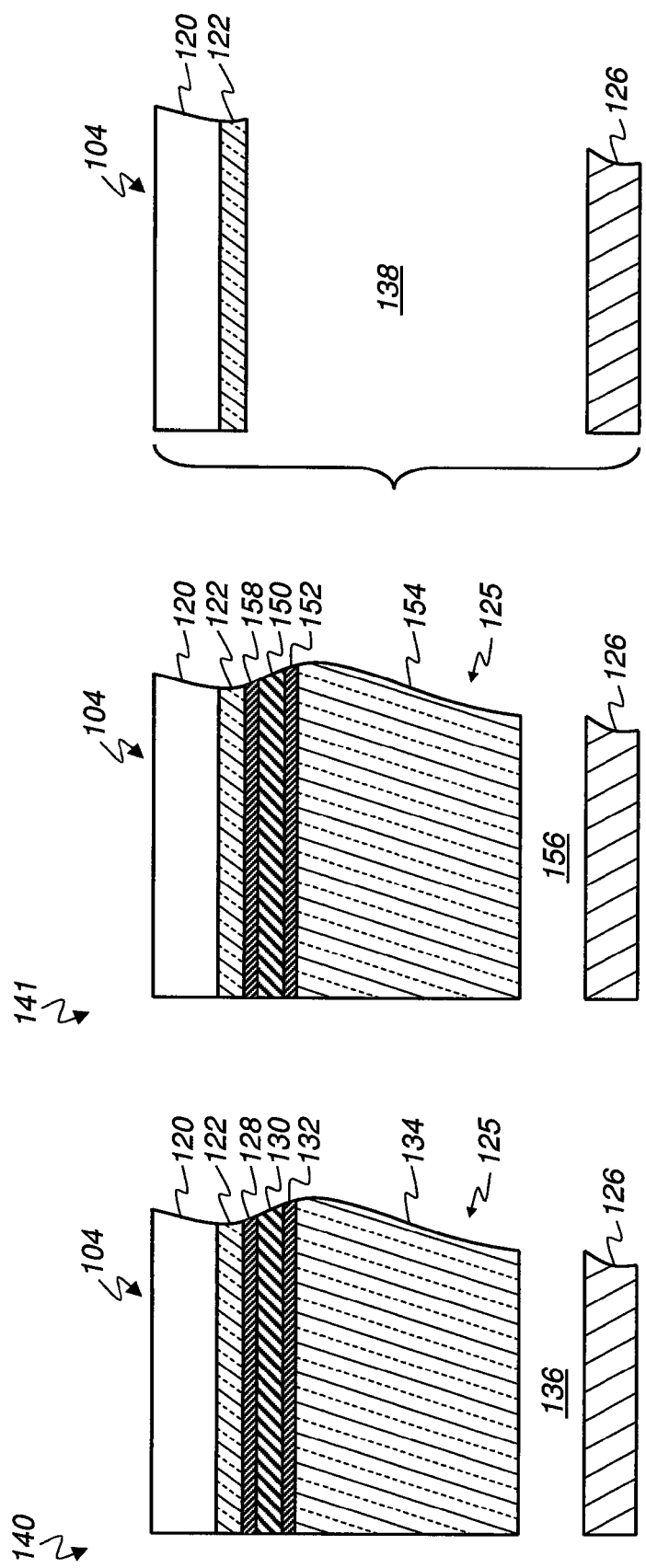

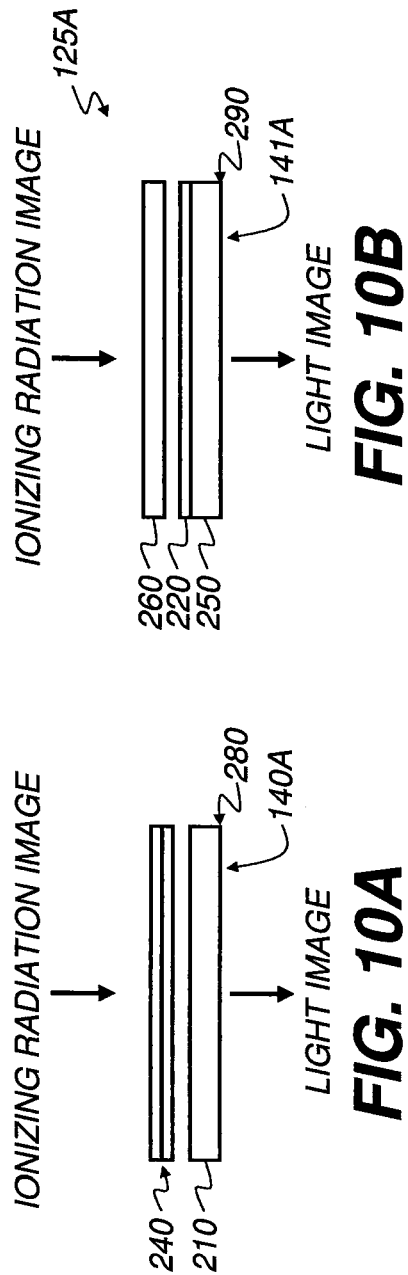
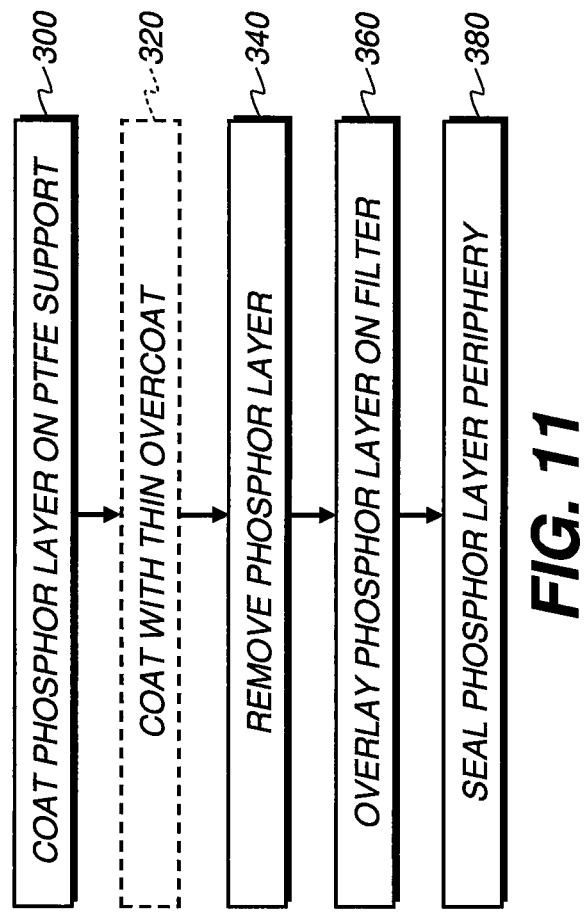

US 8,050,735 B2

APPARATUS AND METHOD FOR MULTI-MODAL IMAGING

CROSS REFERENCE TO RELATED APPLICATIONS

Priority is claimed from commonly assigned provisional U.S. Patent Application Ser. No. 61/024,621 filed Jan. 30, 2008 by Feke et al., entitled APPARATUS AND METHOD FOR MULTI-MODAL IMAGING.

This application is a continuation-in-part of commonly assigned U.S. patent application Ser. No. 11/221,530 filed Sep. 8, 2005 by Vizard et al., entitled APPARATUS AND METHOD FOR MULTI-MODAL IMAGING, which issued on Jun. 8, 2010 as U.S. Pat. No. 7,734,325.

The disclosures of both applications are hereby incorporated by reference in this application.

FIELD OF THE INVENTION

The invention relates generally to the field of imaging systems, and particularly to the imaging of objects. More specifically, the invention relates to an apparatus and method that enable analytical imaging of objects (for example, small animals and tissue) in differing modes, including bright-field, dark-field (e.g., luminescence and fluorescence), and x-ray and radioactive isotopes.

BACKGROUND OF THE INVENTION

Electronic imaging systems are well known for enabling molecular imaging. A perspective view of an exemplary electronic imaging system 10 is shown in FIG. 1 and a diagrammatic view of such system is shown in FIG. 2. The illustrated system is the KODAK Image Station 2000MM Multimodal Imaging System. System 10 includes a light source 12, an optical compartment 14, an optional mirror 16 within compartment 14, a lens and camera system 18, and a communication and computer control system 20 which can include a display device 22 such as a computer monitor. Lens and camera system 18 can include an emission filter wheel, not illustrated, for fluorescent imaging. Light source 12 can include an excitation filter selector, not illustrated, for fluorescent excitation or bright field color imaging. In operation, an image of an object is captured using lens and camera system 18 which converts the light image into an electronic image, which can be digitized. The digitized image can be displayed on display device 22, stored in memory, transmitted to a remote location, processed to enhance the image, and/or used to print a permanent copy of the image.

Reference is made to the previously mentioned application of Vizard et al. that discloses an imaging system for imaging an object. The imaging system includes a support member adapted to receive the object in an immobilized state. The system also includes first means for imaging the immobilized object in a first imaging mode to capture a first image, and second means for imaging the immobilized object in a second imaging mode, different from the first imaging mode, to capture a second image. The first imaging mode is selected from the group: x-ray mode and radio isotopic mode. The second imaging mode is selected from the group: bright-field mode and dark-field mode. A removable phosphor screen or panel is employed when the first image is captured but is not employed when the second image is captured. The phosphor screen or panel is adapted to respond to ionizing radiation during an x-ray mode or a radio isotopic mode by emitting visible light that is detected by the first means for imaging. The screen or panel is removable from the imaging system for the bright-field mode or dark-field mode, but without moving the immobilized object or support member. The system can further include means for generating a third image comprised of the first and second image. Reference also is made to commonly assigned U.S. Pat. No. 6,444,988 by Vizard, incorporated herein by reference.

SUMMARY OF THE INVENTION

An object of the present invention is to provide an apparatus and method for enabling analytical imaging of an object in three or more differing imaging modes.

This object is given only by way of illustrative example, and such object may be exemplary of one or more embodiments of the invention. Other desirable objectives and advantages inherently achieved by the disclosed invention may occur or become apparent to those skilled in the art. The invention is defined by the claims.

A system for imaging an object in accordance with one embodiment of the present invention includes a support member adapted to receive the object in an immobilized state; first means for imaging the immobilized object in a first imaging mode to capture a first image; second means for imaging the immobilized object in a second imaging mode, different from the first imaging mode, to capture a second image; and third means for imaging the immobilized object in a third imaging mode, different from the first and second imaging modes, to capture a third image.

The first imaging mode is for high resolution imaging applications of (a) ionizing radiation such as x-ray radiation or (b) low energy, self-attenuating ionizing radiation such as electrons or beta particles from radioactive isotope decay.

The second imaging mode is for high sensitivity imaging applications using ionizing radiation such as high energy electrons or gamma rays from radioactive isotope decay.

The third imaging mode is for imaging applications using bright-field imaging and/or dark-field imaging. A removable phosphor plate assembly is provided that includes a plurality of phosphor panels, such as a first phosphor panel for the first imaging mode and an adjacent second phosphor panel for the second imaging mode.

The phosphor plate assembly is employed and positioned for capture of each of the first two images but is not employed for capture of the third image. Separate, interchangeable phosphor plate assemblies with single phosphor panels also could be used for the first and second imaging modes, without departing from the invention. The first phosphor panel is adapted to respond to ionizing radiation by emitting visible light, where the ionizing radiation is x-ray radiation or low-energy electrons or beta particles from radioactive isotope decay. Thus, the first phosphor panel is optimized for high spatial resolution. The second phosphor panel also is adapted to respond to ionizing radiation by emitting visible light, but where the ionizing radiation is high energy ionizing radiation such as high-energy electrons or gamma rays from radioactive isotope decay. Thus, the second phosphor panel is optimized for sensitivity to incident radiation. The phosphor plate assembly and its panel or panels are adapted to be removable from the imaging path without moving the immobilized object or its support member. The system can further include fourth means for generating a fourth image comprised of any combination of the first, second, and third images.

Various advantages are provided by the apparatus and method of the invention. The embodiments of the invention provide at least three imaging modes: a first mode for imaging non-ionizing, optical radiation, such as bright-field mode, fluorescence mode and luminescence mode; a second mode for imaging ionizing radiation optimized for high resolution; and a third mode for imaging ionizing radiation optimized for high sensitivity. The apparatus and method of the invention provide improved, greater flexibility with minimal complexity due to use of a phosphor screen assembly having at least two phosphor panels, one for high resolution and one for high sensitivity, that can be moved selectively into the imaging path without disturbing the immobilized object. The invention enables precise co-registration of at least three images captured using different modes. The improved flexibility and precise co-registration provided by the invention also facilitate application of multi-modal imaging probes; that is, probes containing both fluorescent and radio isotopic agents. For example, near infrared (NIR) monomolecular multimodal imaging agents comprising a heptamethine carbocyanine and a chelate between indium and 1,4,7,10-tetraazacyclododecane-N,N',N'',N'''-tetraacetic acid, $H_4L$ as described in an article entitled "Monomolecular Multimodal Fluorescence-Radioisotope Imaging Agents" by Zhang et al, *Bioconjugate Chemistry*, 16 (5), 1232-1239, 2005. The agents disclosed by Zhang et al are useful for diagnosis of diseases by different imaging methods, thereby providing complementary information about the functional status of diseased tissues or organs while considering images from the different imaging modalities with a high degree of accuracy.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 1 shows a perspective view of an exemplary prior art electronic imaging system.

FIG. 2 shows a diagrammatic view of the electronic imaging system of FIG. 1.

FIG. 3A shows a diagrammatic side view of an imaging system in accordance with the present invention.

FIG. 3B shows a diagrammatic front view of the imaging system of FIG. 3A.

FIG. 5A shows a diagrammatic side view of a sample object stage and movable phosphor plate assembly according to the invention.

FIG. 5B shows a diagrammatic side view of the sample object stage in a first imaging position P1 wherein the phosphor plate assembly is disposed proximate the sample object stage and positioned for imaging of the first phosphor panel.

FIG. 5C shows a diagrammatic side view of the sample object stage in a second imaging position P2 wherein the phosphor plate assembly is disposed proximate the sample object stage and positioned for imaging of the second phosphor panel.

FIG. 5D shows a diagrammatic side view of the sample object stage in a third imaging position P3 wherein the phosphor plate assembly is not proximate the sample object stage.

FIG. 6 shows an enlarged, fragmentary sectional view taken along line 6-6 of FIG. 5B.

FIG. 7 shows an enlarged, fragmentary sectional view taken along line 7-7 of FIG. 5C.

FIG. 8 shows an enlarged, fragmentary sectional view taken along line 8-8 of FIG. 5D.

FIGS. 10A and 10B show diagrammatic views of a phosphor panels suitable for use with the apparatus and method of the present invention.

FIG. 11 is a flow diagram of a method for making the phosphor panels of FIGS. 10A and 10A.

DETAILED DESCRIPTION OF THE INVENTION

Figure 4:
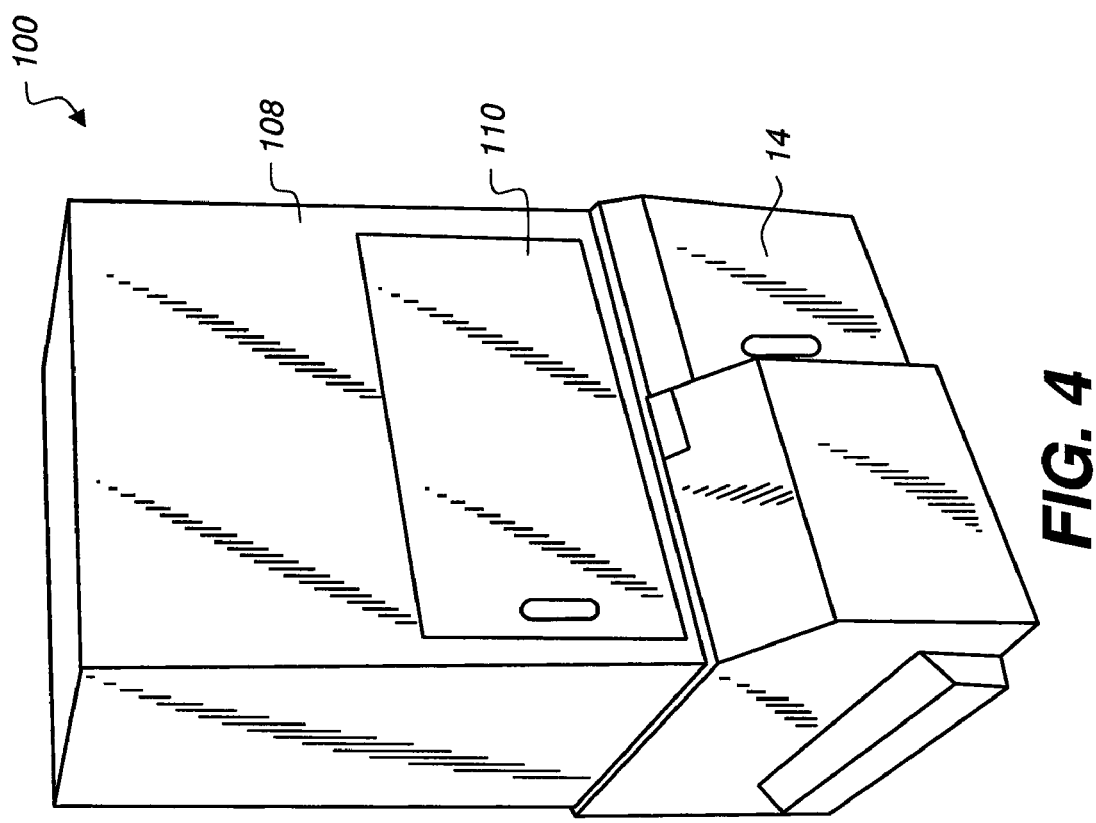
FIG. 4 shows a perspective view of the imaging system of FIGS. 3A and 3B.

The invention will be described in detail with particular reference to certain embodiments thereof, but it will be understood that variations and modifications can be effected within the spirit and scope of the invention. The following is a detailed description of certain embodiments of the invention, reference being made to the drawings in which the same reference numerals identify the same elements of structure in each of the several figures.

The inventors have recognized that the complex pharmaceutical analyses of images of small objects or subjects, such as small animals and small volumes of tissue, can be particularly enhanced by using three or more different in-vivo imaging modalities to produce three or more images than can be analyzed separately or co-registered for analysis. Using the known practices of bright-field, dark-field, radiographic, and radioactive isotope imaging for the analysis of small objects or subjects, such as a mouse, can be expensive and may not provide the precision of co-registered images that is desired.

Using the apparatus and method of the present invention, precisely co-registered fluorescent, luminescent and/or isotopic probes within an object (e.g., a live animal and tissue) can be localized; and multiple images can be accurately overlaid onto a simple bright-field reflected image or anatomical x-ray of the same animal within minutes of animal immobilization.

The present invention uses the same imaging system to capture three or more images using differing modes of imaging, thereby enabling simplified multi-modal imaging. In addition, the relative movement of probes can be kinetically resolved over the time period that the animal is effectively immobilized, which can be tens of minutes. Alternatively, the same animal may be subject to repeated complete image analysis over a period of days or weeks required to assure completion of a pharmaceutical study, with the assurance that the precise anatomical frame of reference (particularly, the x-ray) may be readily reproduced upon repositioning the object animal. The method of the present invention can be applied to other objects and/or complex systems subject to simple planar imaging methodologies.

More particularly, using the imaging system of the present invention, an immobilized object can be imaged in several imaging modes without changing or moving the immobilized object. These acquired multi-modal images can then be merged to provide a co-registered image for analysis.

Imaging modes supported by the apparatus and method of the present invention include: x-ray imaging, bright-field imaging, dark-field imaging (including luminescence imaging, fluorescence imaging) and radioactive isotope imaging. Radioactive isotope imaging used for the previously mentioned first imaging mode would use low energy electrons or beta rays for high resolution; and for the previously mentioned second imaging mode would use high energy electrons or gamma rays for high sensitivity. Images acquired in these modes can be merged in various combinations for analysis. For example, an x-ray image of the object can be merged with a near infrared (NIR) fluorescence image of the object and a high energy radioactive isotope image of the object to provide a new image for analysis.

The apparatus of the present invention is now described with reference to FIGS. 3A, 3B, and 4. FIG. 3A shows a diagrammatic side view of an imaging system 100 that includes light source 12, optical compartment 14, lens and camera system 18, and communication and computer control system that may include a display device such as a computer monitor. Camera and lens system 18 can include an emission filter wheel for fluorescent imaging, not illustrated. Light source 12 can include an excitation filter selector for fluorescent excitation or bright field color imaging, not illustrated. Imaging system 100 may include an x-ray source 102 and a support member such as a sample object stage 104. An object such as an immobilized mouse is received on and supported by stage 104 in use of system 100. System 100 also may include epi-illumination, for example, using fiber optics 106, which directs conditioned light (of appropriate wavelength and divergence) toward sample object stage 104 to provide bright-field or fluorescent imaging. Sample object stage 104 is disposed within a sample environment 108, which allows access to the object being imaged. In one embodiment, sample environment 108 is light-tight and fitted with light-locked gas ports, not illustrated, for environmental control. Environmental control enables practical x-ray contrast below 8 KeV (air absorption) and aids in life support for biological specimens. An access means or member 110 may be included to provide convenient, safe and light-tight access to sample environment 108, such as a door, opening, labyrinth, and the like. Additionally, sample environment 108 may be adapted to provide atmospheric control for sample maintenance or soft x-ray transmission, such as temperature and humidity controls, sources of alternative gases, and the like. Imaging system 100 can be a unitary system. Alternatively, imaging system 100 can be a modular unit adapted to be used or mated with electronic imaging system such as electronic imaging system 10.

FIGS. 5-7 more particularly illustrate elements of sample object stage 104 and an optical interface relative with the focal plane of camera and lens system 18. FIG. 5A shows a diagrammatic side view of sample object stage 104 and illustrates movement of an inventive phosphor plate assembly 125 relative to the sample object stage. Phosphor plate assembly 125 may include a plurality of phosphor panels having different characteristics. FIG. 5B shows a diagrammatic side view of the sample object stage in a first imaging position P1 wherein phosphor plate assembly 125 is disposed proximate the sample object stage and positioned for imaging of a first phosphor panel 140 comprised in assembly 125. FIG. 5C shows a diagrammatic side view of the sample object stage in a second imaging position P2 wherein phosphor plate assembly 125 is disposed proximate the sample object stage and positioned for imaging of a second phosphor panel 141, also comprised in assembly 125. Additional phosphor panels may be included in assembly 125. FIG. 5D shows a diagrammatic side view of the sample object stage in the third imaging position P3 wherein phosphor plate assembly 125 has been withdrawn to a position outside the imaging path where neither panel 140 nor panel 141 is proximate the sample object stage. FIG. 6 shows a diagrammatic side view of a section taken along line 6-6 of FIG. 5B, which corresponds with the first imaging position P1. FIG. 7 shows a diagrammatic side view of a section taken along line 7-7 of FIG. 5C, which corresponds with the second imaging position P2. FIG. 8 shows a diagrammatic side view of a section taken along line 8-8 of FIG. 5D, which corresponds with the third imaging position P3.

Continuing with regard to FIGS. 5-8, sample object stage 104 includes a support member made up from an open, typically rectangular frame 120 of metal or plastic, for example, on which is stretched a thin plastic support sheet 122. Support sheet 122 is selected so as to support the weight of an object to be imaged and is made from a material that is optically clear and free of significant interfering fluorescence, such as Mylar, as will be discussed later in this specification.

Phosphor plate assembly 125 is mounted suitably for motion toward and away from sample object stage 104, such as on guide rails or rollers, not illustrated. While those skilled in the art might recognize other configurations, in one embodiment, phosphor plate assembly 125 is mounted for sliding translation in the direction of arrow A relative to frame 120, beneath the sample and in intimate contact with the underside of support sheet 122, as illustrated. As will be more particularly described below, in first imaging position P1, first phosphor panel 140 in phosphor plate assembly 125 is positioned directly opposite and proximate sample object stage 104. In imaging position P1, a high resolution image of the object is captured using x-ray radiation or low-energy electron or beta particle radiation from radioactive isotope decay. In imaging position P2, second phosphor panel 141 in phosphor plate assembly 125 is positioned directly opposite and proximate sample object stage 104. In imaging position P2, a high sensitivity image of the object is captured using a high-energy electron or gamma-ray radiation. Third imaging position P3 is defined when phosphor plate assembly 125 is translated or moved away from sample object stage 104, as shown in FIG. 6D. In position P3, capture of an image of the object can be achieved while phosphor plate 125 is not imaged.

FIG. 6 provides an enlarged, sectional view of sample object stage 104, with phosphor plate assembly 125 in position P1 to more particularly show a preferred focal plane for lens and camera system 18. Sample support sheet 122 may comprise Mylar or polycarbonate and has a nominal thickness of about 0.1 mm. An optional protective layer 128, such as a thin sheet or layer of polyester or polycarbonate of about 0.025 mm thickness may be provided on phosphor panel 140 to protect the panel surfaces during movement past support sheet 122. Protective layer 128 also may promote or increase the image-forming light output. In one embodiment, protective layer 128 may be reflective so as to prevent object reflection back into the image-forming panels, reducing the confusion of the ionizing radiation image.

Panel 140 further comprises a phosphor layer 130 that responds to ionizing radiation by emitting visible light that practically can be managed by lens and camera system 18, such as a CCD camera. Phosphor layer 130 can have a thickness ranging from about 0.01 mm to about 0.1 mm, suitable for high resolution imaging using x-ray radiation or low-energy electron or beta particle radiation from radioactive isotope decay. On the underside of phosphor layer 130, as illustrated, an optical layer 132 may be provided for conditioning emitted light from phosphor layer 130. Optical layer 132 can have a thickness in the range of less than about 0.001 mm. Particular information about phosphor layer 130 and optical layer 132 is disclosed in U.S. Pat. No. 6,444,988 previously mentioned. The focal plane for lens and camera system 18 may be at the underside of layer 130. A supporting glass plate 134 is provided for phosphor panel 140. Glass plate 134 is spaced at a suitable mechanical clearance from an optical platen 126, for example, by an air gap or void 136. In one embodiment, the surfaces of clear optical media, such as a lower surface of glass plate 134 and both surfaces of optical platen 126, are provided with anti-reflective coatings to minimize reflections that may confuse the images of the object.

FIG. 7 provides an enlarged, sectional view of sample object stage 104 with phosphor plate assembly 125 in position P2 to more particularly show a preferred focal plane for lens and camera system 18. An optional protective layer 158, such as reflective Mylar of about 0.025 mm thickness, may be provided on phosphor panel 141 to protect the panel surfaces during movement. Protective layer 158 also may promote or increase the image-forming light output. In one embodiment, protective layer 158 may be reflective so as to prevent object reflection back into the image-forming panels, reducing the confusion of the ionizing radiation image.

Panel 141 further comprises a phosphor layer 150 that responds to ionizing radiation by emitting visible light that practically can be managed by lens and camera system 18, such as a CCD camera. Phosphor layer 150 can have a thickness ranging from about 0.01 mm to about 0.1 mm, suitable for high sensitivity imaging using high-energy electron or gamma-ray radiation from radioactive isotope decay. On the underside of phosphor layer 150, as illustrated, an optical layer 152 may be provided for conditioning emitted light from phosphor layer 150. Optical layer 152 can have a thickness in the range of less than about 0.001 mm. Particular information about phosphor layer 150 and optical layer 152 is disclosed in U.S. Pat. No. 6,444,988 previously mentioned. The focal plane for lens and camera system 18 may be at the underside of layer 150. A supporting glass plate 154 is provided for phosphor panel 141. Glass plate 154 is spaced at suitable mechanical clearance from optical platen 126, for example, by an air gap/void 156. In one embodiment, the lower surface of glass plate 154 may be provided with anti-reflective coating to minimize reflections that may confuse the images of the object. Phosphor panels 140 and 141 preferably are comprised in the illustrated, single phosphor plate assembly 125. However, those skilled in the art will understand that separate, independently movable phosphor plate assemblies with single phosphor panels similar to panels 140, 141 (not illustrated) also could be used, without departing from the invention.

FIG. 8 provides an enlarged, sectional view of sample object stage 104 with phosphor plate assembly 125 in position P3, where it is fully removed from the object stage, leaving an air gap or void 138 between object stage 104 and optical platen 126.

Figure 9:
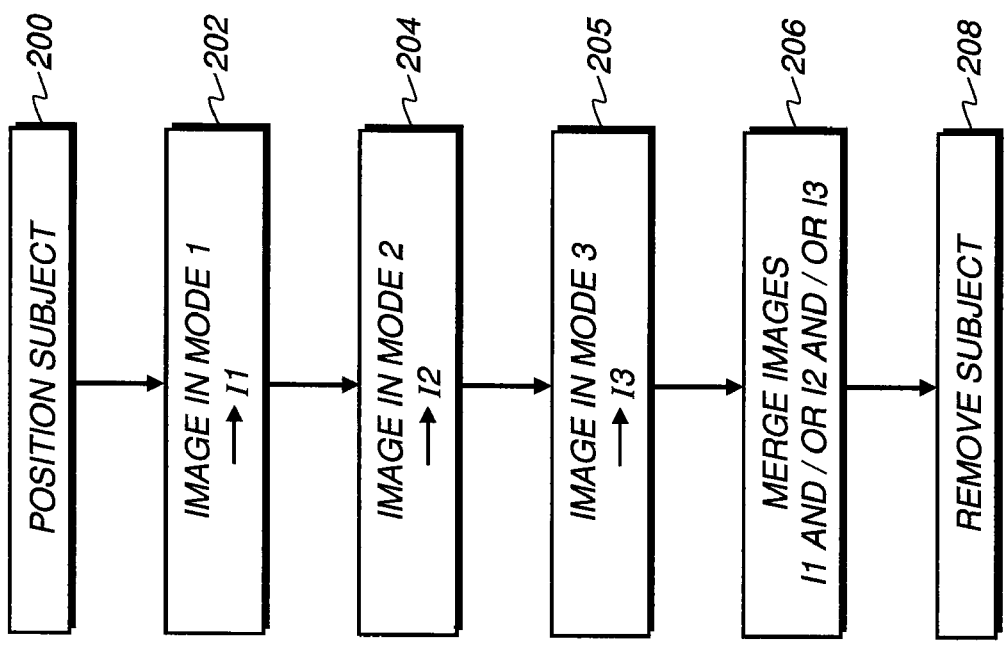
FIG. 9 shows a work flow diagram in accordance with a method of the present invention.

Referring now to FIG. 9, in operation, at step 200 an object (such as a small animal) is immobilized on sample object stage 104. An operator configures system 100 for imaging in a first mode; and at step 202 an image of the object is captured using lens and camera system 18 in the first mode. System 18 converts the light image into an electronic image, which can be digitized. This digitized image is referred to in FIG. 9 as Image1 or I1. The digitized image can be displayed on the display device, stored in memory, transmitted to a remote location, processed to enhance the image, and/or used to print a permanent copy of the image. The object remains immobilized on sample object stage 104; no change in the position/location of the object is made. The operator configures system 100 for imaging in a second mode; and at step 204 an image of the object is captured using system 18 in the second mode. The resulting digitized image is referred to in FIG. 9 as Image2 or I2. The digitized image can be displayed on the display device 22, stored in memory, transmitted to a remote location, processed to enhance the image, and/or used to print a permanent copy of the image. The object remains immobilized on sample object stage 104; no change in the position/location of the object is made. The operator configures system 100 for imaging in a third mode; and at step 205 an image of the object is captured using 18 in the third mode. The resulting digitized image is referred to in FIG. 9 as Image3 or I3.

Since the position of the object was not moved or changed during the capture of the images, any combination of Image1, Image2, and Image3 can readily be merged or superimposed, using methods known to those skilled in the art, such that the images are co-registered. As such, a fourth image can be generated comprising the component images. The images could be combined by a graphical overlay of the molecular images (fluorescence, luminescence or radio isotopic images) upon the anatomical images (x-ray images). The signal levels in the different molecular images would be represented in different color scales in the graphical overlay, in a manner familiar to those skilled in the art, while the signal levels in the anatomical images would be represented by a gray scale. Since the object does not move from image to image, co-registration of images can be done with great accuracy.

As indicated above, system 100 can be configured in several modes, including: x-ray imaging, bright-field imaging, dark-field imaging (including luminescence imaging, fluorescence imaging) and radioactive isotope imaging. To configure system 100 for x-ray imaging or low-energy electron or beta particle imaging, phosphor panel 140 is positioned in optical registration with sample object stage 104 (as shown in FIGS. 5B and 6). In addition, for x-ray imaging, x-ray source 102 is employed to capture the image of the immobilized object. To configure system 100 for high-energy electron or gamma ray imaging, phosphor panel 141 is positioned in optical registration with sample object stage 104 (as shown in FIGS. 5C and 7).

To configure system 100 for bright-field imaging or dark-field imaging (including luminescence imaging and fluorescence imaging), phosphor plate assembly 125 is removed from optical registration with sample object stage 104 (as shown in FIGS. 5D and 8), and an image of the immobilized object is appropriately captured. The object is immobilized on sample object stage 104, and light emitted from the object (usually diffusive within the turbid constituents of a solid object) is projected to the object surface, which intimately bears upon the upper surface of sample support sheet 122.

For the purpose of optical imaging, the object surface is defined by a refractive boundary (e.g., the skin of an animal) that delineates the interior of the object (usually a heterogeneous, turbid media of higher index of refraction) and air. Light emanating from within an object (e.g., luminescent or transmitted) projects to the surface from which it scatters, defining the light that may be productively managed to create an image of the object. Conversely, light may be provided from beneath optical platen 126 and scattered from the object surface, thereby providing reflective light for imaging the same object. For optical imaging, the definition of the object boundary may be moderated by matching the refractive index of the object boundary to support sheet 122 by introducing an index-matching fluid (e.g., water). The depth to which good focus can be achieved in optical imaging is dependent on minimizing the surface scatter of the object, and methods such as index matching and increasing wavelength (e.g., near-infrared, NIR imaging) are well known in the art. The depth to which good focus can be achieved in optical imaging is dependent on minimizing the surface scatter of the object, and methods such as index matching and increasing wavelength (e.g., near-infrared, NIR imaging) are well known in the art.

The emitted sample light can arise from luminescence, fluorescence or reflection, and the focal plane of the lens can be adjusted to the elevation of object surface. Alternatively, the "light" can be ionizing radiation passing through or emitted from the object, or passing into the phosphor and forming an image. Soft x-rays, consistent with thin objects or small animals, project an image through the diffusive phosphor onto the optical boundary, adding the depth of the (more than about 0.02 mm) to the depth of focus. More significant is the focal distance contributed by the phosphor support plate 134, 154 which may be fractional millimeters, depending upon the thickness and index of the glass or plastic. The fractional-millimeter elevation of the best focal plane contributed by the phosphor support can provide a better coincidence between the phosphor focal plane and the focal plane used for optical imaging. For NIR optical imaging, the focal plane may be located at millimeter depths into a nominally turbid object. The phosphor support plate 134, 154 can be thicker to maximize the coincidence of the optical and phosphor imaging planes. Those skilled in the art will recognize how to tune the materials of the present invention to optimally co-locate the optical and phosphor imaging planes. Currently described materials may be practically assembled to assure multi-modal focal plane co-location to accommodate the demands of a fast lens system.

Appropriately fast lens systems for dark-field and x-ray imaging applications will likely have sub-millimeter focal depths, necessitating the above considerations. Accordingly, for a particular embodiment, it may be desirable for multiple optical elements to enable the location of a common focal plane shared by differing modes of imaging.

Emitted gamma rays from a thick object (such as 99Tc emission from an animal organ) are distributed over the plane of the phosphor, diffusing the image by millimeters, and an appropriately thick phosphor layer (about 0.1 mm) may be used to increase detection efficiency. Consequently, the location of the focal plane at the supporting sheet is not critical to the resolution of the radio isotopic image. Better resolution and more precise planar projection of the emitting isotope can be achieved by gamma-ray collimation. Collimators of millimeter-resolution are available and capable of projecting isotopic location to millimeter resolution at the focal plane of the phosphor in the present invention.

Of particular relevance to the operation of the present invention is the thickness of the phosphor layers in the focal plane of the lens of system 18. For example, fast lenses (which are essential elements for the practice of imaging low-light emissions) will have a depth of focus of about 0.5 mm. For good resolution of objects of interest, less than about 0.2 mm of spatial resolution is desirable, and a megapixel CCD camera (cooled) imaging at 100 mm field is suitable. Generally, more resolution is desirable.

Precision registration of the multi-modal image can be accomplished using methods known to those skilled in the art. By placing the object on a thin, stretched optical support that allows phosphor plate assembly 125 to be removed without displacement of the object, co-registered optical imaging is enabled by the same lens/camera system using epi-illumination methodologies at a sufficiently similar focal plane.

Referring now to FIGS. 10A and 10B, there are shown expanded sectional views of a suitable, alternative phosphor plate assembly 125A for use with the apparatus and method of the present invention. Assembly 125A includes a first panel 140A and a second panel 141A, shown separately for ease of illustration. Assembly 125A may include a plurality of phosphor panels having different characteristics. First panel 140A includes a first transparent support 210, such as glass, on which is supported a thin phosphor layer 240. Thin phosphor layer 240 is used for high resolution imaging applications of ionizing radiation or for very low energy (self-attenuating) ionizing radiation such as low-energy electrons or beta particles. Second panel 141A includes a second transparent support 250, such as glass, upon which is coated an interference filter 220 which is a multicoated short-pass filter designed to transmit light at a specified wavelength (and below) and reflect light above that wavelength. For high sensitivity, second panel 141A also includes a thick phosphor layer 260 supported on filter 220. Thick phosphor layer 260 is used for high energy ionizing radiation that freely penetrates the phosphor such as high-energy electrons or gamma rays.

The phosphor used in phosphor layers 240 and 260 in one embodiment is Gadolinium Oxysulfide: Terbium whose strong monochromatic line output (544-548 nanometers (nm)) is ideal for co-application with interference optics. This phosphor has technical superiority regarding linear dynamic range of output, sufficiently "live" or prompt emission and time reciprocity, and intrascenic dynamic range which exceeds other phosphors and capture media. This phosphor layer has a nominal thickness of 10-30 micrometers (μm) at 5-20 grams/square foot (g/ft$^2$) of phosphor coverage, optimally absorbing 10-30 KeV x-rays. Thick phosphor layer 260 has a nominal thickness of 100 μm at 80 g/ft$^2$ of phosphor coverage.

Interference filter 220 transmits light at 551 nm and below and reflects light above that wavelength. Filter 220 comprises layers of Zinc Sulfide-Cryolite that exhibits a large reduction in cutoff wavelength with increasing angle of incidence. The filter has a high transmission at 540-551 nm to assure good transmission of 540-548 nm transmission of the GOS phosphor. The filter also has a sharp short-pass cut-off at about 553 nm, that blue shifts at about 0.6 nm per angular degree of incidence to optimize optical gain.

Glass supports 210 and 250 should be reasonably flat, clear, and free of severe defects. The thickness of supports 210 and 250 can be 2 millimeters. The opposite sides 280 and 290 of glass supports 210 and 250 are coated with anti-reflective layers (such as Magnesium Fluoride, green optimized) to increase transmittance and reduce optical artifacts to ensure that the large dynamic range of the phosphor emittance is captured.

Referring now to FIG. 11, there are shown steps of a method of producing phosphor layer 240. At step 300, a mixture of GOS:Tb in a binder is coated on a polytetrafluoroethylene (PTFE) support. The PTFE support enables release of the coated phosphor layer from the PTFE support and subsequent use of the phosphor layer without support, since conventional supporting materials are an optical burden to phosphor layer performance. For the thin phosphor layer 240, at step 320 an ultra thin (about 0.5 g/ft$^2$, 0.5 μm thick) layer of cellulose acetate overcoat can be applied to offer improved handling characteristics of the thin phosphor layer and to provide greater environmental protection to the underlying optical filter. At step 340, the phosphor layer is removed from the PFTE support. At step 360, the thin phosphor layer over-coated side is overlaid on support 210. Clean assembly of the thin phosphor layer 240 and support 210 assures an optical boundary that optimizes management of phosphor panel light output into the camera of system 18. Optical coupling of layer 240 and support 210 is not necessary, since performance reduction may result. At step 380, layer 240 can be sealed around its periphery and around the periphery of support 210 for mechanical stability and further protection of the critical optical boundary against environmental (e.g., moisture) intrusion.

Advantages of the present invention include: anatomical localization of molecular imaging agent signals in small animals, organs, and tissues; precise co-registration of anatomical x-ray images with optical molecular and radioactive isotope images using one system; improved understanding of imaging agent's bio-distribution through combined use of time lapse molecular imaging with x-ray imaging; and simple switching between multi-wavelength fluorescence, luminescence, radioactive isotope, and x-ray imaging modalities without moving the object or sample.

The invention has been described in detail with particular reference to illustrated embodiments, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST 10 known imaging system
12 light source
14 optical compartment
16 mirror
18 lens and camera system
20 communication/computer control system
22 display device
100 imaging system
102 x-ray source
104 sample object stage
106 fiber optics
108 sample environment
110 access means or member
120 open, rectangular frame
122 support sheet
125, 125A phosphor plate assembly
126 optical platen
128 protective layer
130 phosphor layer
132 optical layer
134 supporting glass plate
136 air gap/void
138 air gap/void
140, 140A first phosphor panel
141, 141A second phosphor panel
150 phosphor layer
152 optical layer
154 supporting glass plate
156 air gap/void
158 protective layer
200-208 Steps in imaging process
210 first transparent support
220 interference filter
240 thin phosphor layer
250 second transparent support
260 thick phosphor layer
280 opposite side
290 opposite side
300-380 Steps in phosphor plate production process
A Arrow showing movement of plate assembly 125
P1, P2, P3 Positions of plate assembly 125 relative to stage 104

What is claimed is:

1. A system for imaging an object, comprising:
a support member adapted to receive the object in an immobilized state;
a movable phosphor plate assembly adapted to respond to ionizing radiation by emitting visible light;
first imaging means for imaging the immobilized object in a first imaging mode to capture a first, high resolution image in a first position of the phosphor plate assembly;
second imaging means for imaging the immobilized object in a second imaging mode, different from the first imaging mode, to capture a second, high sensitivity image in a second position of the phosphor plate assembly; and
third imaging means for imaging the immobilized object in a third imaging mode, different from the first and second imaging modes, to capture a third image in the absence of the phosphor plate,
wherein the first imaging mode uses the phosphor plate assembly and is selected from the group: x-ray mode and low energy radio isotope mode; the second imaging mode uses the phosphor plate assembly and a high energy radio isotope mode, and the third imaging mode is selected from the group: bright-field mode, fluorescence mode and luminescence mode.

2. The system of claim 1, further comprising means for generating a fourth image comprised of any combination of the first, second and third images.

3. The system of claim 1, wherein the phosphor plate assembly comprises first and second phosphor panels, each panel comprising a protective layer; a phosphor layer; and a transparent support layer, the first panel being for the first image and the second panel being for the second image.

4. The system of claim 3, wherein each panel further comprises an optical layer.

5. The system of claim 3, wherein the protective layer is reflective.

6. The system of claim 1, further comprising multiple optical elements to enable the location of a common focal plane shared by the imaging modes.

7. A system for imaging an object, comprising:
a support member adapted to receive the object in an immobilized state;
first means for imaging the immobilized object in a first imaging mode to capture a first image, the first imaging mode being for high resolution imaging applications using ionizing radiation such as x-ray radiation or low energy, self-attenuating ionizing radiation such as electrons or beta particles from radioactive isotope decay;
second means for imaging the immobilized object in a second imaging mode to capture a second image, the second imaging mode being for high sensitivity imaging applications using ionizing radiation such as high-energy electrons or gamma rays from radioactive isotope decay;
third means for imaging the immobilized object in a third imaging mode to capture a third image, the third imaging mode being for imaging applications using bright-field imaging and/or dark-field imaging;
a plurality of phosphor panels including a first phosphor panel movable to a first position proximate the support member for capture of the first image and a second phosphor panel movable to a second position proximate the support member for capture of the second image, and
means for removing the phosphor panels from the positions proximate the support member, without moving the immobilized object, prior to capture of the third image.

8. The system of claim 7, when the first image is captured using x-ray radiation, the first means comprises an x-ray source adapted to transmit x-ray radiation along a path toward the immobilized object to capture the x-ray image of the immobilized object.

9. The system of claim 7, further comprising means for generating a fourth image comprised of any combination of the first, second, and third images.

10. The system of claim 9, further comprising means for displaying, transmitting, processing, or printing, the fourth image.

11. The system of claim 7, wherein the first and second phosphor panels each comprises a protective layer; a phosphor layer; and a transparent support layer.

12. The system of claim 11, wherein each panel further comprises an optical layer.

13. The system of claim 11, wherein the protective layers are reflective.

14. The system of claim 7, wherein the multiple optical elements enable the location of a common focal plane shared by differing modes of imaging.

15. The system of claim 7, wherein the first and second phosphor panels are independently movable.

16. A method of imaging an object, comprising the steps of:
providing a support member adapted to receive the object in an immobilized state,
providing a phosphor plate assembly disposed proximate the support member in a first position for capturing a first image;
imaging the immobilized object in a first imaging mode to capture a first image, the first imaging mode being for high resolution imaging applications using ionizing radiation such as x-ray radiation or low energy, self-attenuating ionizing radiation such as electrons or beta particles from radioactive isotope decay,
moving the phosphor plate assembly until it is disposed proximate the support member in a second position for capturing a second image;
imaging the immobilized object in a second imaging mode to capture a second image, the second imaging mode being for high sensitivity imaging applications using radiation such as high-energy electrons or gamma rays from radioactive isotope decay;
moving the phosphor plate assembly from the second position to a third position not proximate the support member, and
imaging the immobilized object in a third imaging mode to capture a third image, the third imaging mode being for imaging applications using bright-field imaging and/or dark-field imaging.

17. The method of claim 16, further comprising the step of generating a fourth image comprised of any combination of the first, second, and third images.

18. The method of claim 17, further comprising the step of displaying, transmitting, processing, or printing, the fourth image.

19. A method of imaging an object, comprising the steps of:
providing a support member adapted to receive the object in an immobilized state;
providing a phosphor plate assembly comprising a first panel and a second panel, movable relative to the support member, without disturbing the immobilized object, between a first position wherein the first panel is in optical registration with the support member, a second position wherein the second panel is in optical registration with the support member, and a third position wherein the phosphor plate is not in optical registration with the support member;
capturing a high resolution x-ray image or an isotopic image of the immobilized object when the phosphor plate in disposed in the first position;
capturing a high sensitivity isotopic image of the immobilized object when the phosphor plate in disposed in the second position; and
capturing a dark-field image or a bright-field image of the immobilized object when the phosphor plate is disposed in the third position.

20. The method of claim 19, further comprising the steps of: generating a fourth image comprised of any combination of the first, second, and third images; and displaying, transmitting, processing, or printing, the fourth image.

* * * * *